(12) United States Patent (10) Patent No.: US 7,517,166 B2
Keck (45) Date of Patent: Apr. 14, 2009

(54) APPLICATOR WITH DISCRETE POCKETS OF A COMPOSITION TO BE DELIVERED WITH USE OF THE APPLICATOR

(75) Inventor: Laura E. Keck, Alpharetta, GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 539 days.

(21) Appl. No.: 11/193,643

(22) Filed: Jul. 29, 2005

(65) Prior Publication Data

US 2007/0025797 A1    Feb. 1, 2007

(51) Int. Cl.
    *A46B 5/04* (2006.01)
(52) U.S. Cl. ............................ 401/7; 401/201
(58) Field of Classification Search ............ 401/7, 401/132–135, 201, 196, 261; 604/1–3
    See application file for complete search history.

(56) References Cited

U.S. PATENT DOCUMENTS

| 1,161,719 | A | * | 11/1915 | Norton ............ 401/7 |
| 1,896,941 | A | | 2/1933 | Cohen |
| 2,041,262 | A | | 5/1936 | Ness |
| 2,076,681 | A | | 4/1937 | Steinmayer |
| 2,122,482 | A | | 7/1938 | Marr et al. |
| 2,179,614 | A | | 11/1939 | Cohen |
| 2,599,191 | A | | 6/1952 | Meunier |
| 2,646,796 | A | | 7/1953 | Scholl |
| 2,673,365 | A | | 3/1954 | Moor, Jr. |
| 2,882,528 | A | | 4/1959 | Tassie |
| 2,925,605 | A | | 2/1960 | Wheeler |
| 2,966,691 | A | | 1/1961 | Cameron |
| 3,070,102 | A | | 12/1962 | MacDonald |
| 3,124,824 | A | | 3/1964 | Lutz |
| 3,263,681 | A | | 8/1966 | Nechtow et al. |
| 3,280,420 | A | | 10/1966 | Wanzenberg |
| 3,298,507 | A | | 1/1967 | Micciche |
| 3,338,992 | A | | 8/1967 | Kinney |
| 3,341,394 | A | | 9/1967 | Kinney |
| 3,348,541 | A | | 10/1967 | Loebeck |
| 3,368,668 | A | | 2/1968 | Micciche |
| 3,448,478 | A | | 6/1969 | Nash et al. |

(Continued)

FOREIGN PATENT DOCUMENTS

DE    19620487    11/1997

(Continued)

OTHER PUBLICATIONS

*Polymer Blends & Composites*; John A. Manson & Leslie H. Sperling © 1976; Plenum Press; IBSN: 0-306-30821-2; pp. 273-277.

(Continued)

*Primary Examiner*—David J Walczak
(74) *Attorney, Agent, or Firm*—Dority & Manning, P.A.

(57) ABSTRACT

An applicator includes a tubular structure having a front panel that includes a liquid impermeable material and an outer liquid permeable cover material. A plurality of discrete pockets are formed between the cover material and the liquid impermeable material. A composition is contained within the pockets and, in use of the wipe, the composition migrates through the cover material during use of the applicator.

18 Claims, 5 Drawing Sheets

U.S. PATENT DOCUMENTS

| | | | |
|---|---|---|---|
| 3,485,706 | A | 12/1969 | Evans |
| 3,502,763 | A | 3/1970 | Hartman |
| 3,542,615 | A | 11/1970 | Dobo et al. |
| 3,589,823 | A | 6/1971 | Hendrickson |
| 3,675,264 | A | 7/1972 | Storandt |
| 3,692,618 | A | 9/1972 | Dorschner |
| 3,696,821 | A | 10/1972 | Adams, IV |
| 3,802,817 | A | 4/1974 | Matsuki et al. |
| 3,849,241 | A | 11/1974 | Butin et al. |
| 3,853,412 | A | 12/1974 | Griffin |
| 3,855,046 | A | 12/1974 | Hansen et al. |
| 3,902,509 | A | 9/1975 | Tundermann et al. |
| 3,905,113 | A | 9/1975 | Jacob |
| 3,952,867 | A | 4/1976 | McCord |
| 3,982,298 | A | 9/1976 | Ota |
| 4,041,203 | A | 8/1977 | Brock et al. |
| 4,084,586 | A | 4/1978 | Hettick |
| 4,100,324 | A | 7/1978 | Anderson et al. |
| 4,121,312 | A | 10/1978 | Penney |
| 4,269,181 | A | 5/1981 | Delannoy |
| 4,323,534 | A | 4/1982 | DesMarais |
| 4,333,979 | A | 6/1982 | Sciaraffa et al. |
| 4,335,731 | A | 6/1982 | Bora, Jr. |
| 4,340,563 | A | 7/1982 | Appel |
| 4,414,970 | A | 11/1983 | Berry |
| 4,616,374 | A | 10/1986 | Novogrodsky |
| 4,617,694 | A | 10/1986 | Bori |
| 4,643,725 | A | 2/1987 | Schlesser et al. |
| 4,643,791 | A | 2/1987 | Jurrius et al. |
| 4,657,802 | A | 4/1987 | Morman et al. |
| 4,660,228 | A | 4/1987 | Ogawa et al. |
| 4,663,220 | A | 5/1987 | Wisneski et al. |
| 4,665,901 | A | 5/1987 | Spector |
| 4,707,398 | A | 11/1987 | Boggs |
| 4,720,415 | A | 1/1988 | Vander Wielen et al. |
| 4,724,184 | A | 2/1988 | Killian et al. |
| 4,733,410 | A | 3/1988 | Glotkin |
| 4,741,949 | A | 5/1988 | Morman et al. |
| 4,766,029 | A | 8/1988 | Brock et al. |
| 4,781,966 | A | 11/1988 | Taylor |
| 4,789,699 | A | 12/1988 | Kieffer et al. |
| 4,797,310 | A | 1/1989 | Barby et al. |
| 4,803,117 | A | 2/1989 | Daponte |
| 4,818,464 | A | 4/1989 | Lau |
| 4,820,572 | A | 4/1989 | Killian et al. |
| 4,825,470 | A | 5/1989 | Horio |
| 4,828,556 | A | 5/1989 | Braun et al. |
| 4,834,738 | A | 5/1989 | Kielpikowski et al. |
| 4,858,245 | A | 8/1989 | Sullivan et al. |
| 4,875,247 | A | 10/1989 | Berg |
| 4,884,581 | A | 12/1989 | Rescigno |
| 4,920,974 | A | 5/1990 | Roth et al. |
| 4,923,742 | A | 5/1990 | Killian et al. |
| 4,926,851 | A | 5/1990 | Bulley |
| 4,965,122 | A | 10/1990 | Morman |
| D313,317 | S | 1/1991 | Brunner et al. |
| 4,981,747 | A | 1/1991 | Morman |
| 4,998,978 | A | 3/1991 | Varum |
| 5,036,551 | A | 8/1991 | Dailey et al. |
| 5,057,368 | A | 10/1991 | Largman et al. |
| 5,068,941 | A | 12/1991 | Dunn |
| 5,093,422 | A | 3/1992 | Himes |
| 5,108,820 | A | 4/1992 | Kaneko et al. |
| 5,108,827 | A | 4/1992 | Gessner |
| 5,114,781 | A | 5/1992 | Morman |
| 5,116,662 | A | 5/1992 | Morman |
| 5,120,758 | A | 6/1992 | Satoh |
| 5,123,113 | A | 6/1992 | Smith |
| 5,133,971 | A | 7/1992 | Copelan et al. |
| 5,169,706 | A | 12/1992 | Collier, IV et al. |
| 5,181,914 | A | 1/1993 | Zook |
| 5,213,428 | A | 5/1993 | Salman |
| 5,226,992 | A | 7/1993 | Morman |
| 5,228,433 | A | 7/1993 | Rosen |
| 5,277,976 | A | 1/1994 | Hogle et al. |
| 5,280,661 | A | 1/1994 | Brown |
| 5,283,924 | A | 2/1994 | Kaminski et al. |
| 5,287,584 | A | 2/1994 | Skinner |
| 5,294,482 | A | 3/1994 | Gessner |
| 5,304,599 | A | 4/1994 | Himes |
| 5,320,531 | A | 6/1994 | Delizo-Madamba |
| 5,332,613 | A | 7/1994 | Taylor et al. |
| 5,336,545 | A | 8/1994 | Morman |
| 5,336,552 | A | 8/1994 | Strack et al. |
| 5,348,153 | A | 9/1994 | Cole |
| 5,356,005 | A | 10/1994 | Burrello |
| 5,362,306 | A | 11/1994 | McCarver et al. |
| 5,382,400 | A | 1/1995 | Pike et al. |
| 5,383,846 | A | 1/1995 | Short |
| 5,389,202 | A | 2/1995 | Everhart et al. |
| 5,439,487 | A | 8/1995 | Stanitzok |
| 5,440,774 | A | 8/1995 | Cole |
| 5,445,825 | A | 8/1995 | Copelan et al. |
| 5,464,688 | A | 11/1995 | Timmons et al. |
| 5,466,410 | A | 11/1995 | Hills |
| 5,474,525 | A | 12/1995 | Blott |
| 5,486,381 | A | 1/1996 | Cleveland et al. |
| 5,487,201 | A | 1/1996 | Hansen et al. |
| 5,502,863 | A | 4/1996 | Perkins |
| 5,503,908 | A | 4/1996 | Faass |
| 5,507,641 | A | 4/1996 | Cline |
| 5,524,764 | A | 6/1996 | Kaufman et al. |
| 5,529,665 | A | 6/1996 | Kaun |
| 5,541,388 | A | 7/1996 | Gadd |
| 5,554,076 | A | 9/1996 | Clark |
| 5,591,510 | A | 1/1997 | Junker et al. |
| 5,636,405 | A | 6/1997 | Stone et al. |
| 5,678,273 | A | 10/1997 | Porcelli |
| 5,752,926 | A | 5/1998 | Larson et al. |
| 5,765,252 | A | 6/1998 | Carr |
| 5,766,248 | A | 6/1998 | Donovan |
| 5,770,229 | A | 6/1998 | Tanihara et al. |
| 5,771,522 | A | 6/1998 | Carmody |
| 5,794,774 | A | 8/1998 | Porcelli |
| 5,804,021 | A | 9/1998 | Abuto et al. |
| 5,806,668 | A * | 9/1998 | Bixby ................. 15/227 |
| 5,819,765 | A | 10/1998 | Mittiga |
| 5,826,599 | A | 10/1998 | Adams |
| 5,834,002 | A | 11/1998 | Athanikar |
| 5,875,513 | A | 3/1999 | Reinold |
| 5,909,739 | A | 6/1999 | Masrour-Rad |
| 5,911,319 | A | 6/1999 | Porcelli et al. |
| 5,953,783 | A | 9/1999 | Hahn |
| 6,019,773 | A | 2/2000 | Denmark |
| 6,065,480 | A | 5/2000 | Mader |
| 6,105,587 | A | 8/2000 | Dunn |
| 6,112,356 | A | 9/2000 | Hashey |
| 6,139,514 | A | 10/2000 | Benson |
| 6,336,461 | B1 | 1/2002 | Martinez |
| 6,409,059 | B1 | 6/2002 | Calvert |
| 6,420,624 | B1 | 7/2002 | Kawase |
| 6,420,625 | B1 | 7/2002 | Jones et al. |
| 6,494,767 | B2 | 12/2002 | Fisher |
| 6,508,602 | B1 | 1/2003 | Gruenbacher et al. |
| 6,647,549 | B2 | 11/2003 | McDevitt et al. |
| 6,721,987 | B2 | 4/2004 | McDevitt et al. |
| 6,898,819 | B2 | 5/2005 | Tanaka et al. |
| 7,033,100 | B2 * | 4/2006 | Barton et al. ................. 401/7 |
| 2002/0102392 | A1 | 8/2002 | Fish et al. |
| 2003/0050589 | A1 | 3/2003 | McDevitt et al. |

| | | | |
|---|---|---|---|
| 2005/0111898 A1 | 5/2005 | Barton et al. | |

FOREIGN PATENT DOCUMENTS

| | | |
|---|---|---|
| EP | 0303528 | 7/1988 |
| EP | 0638277 A1 | 2/1995 |
| EP | 0985364 A2 | 3/2000 |
| EP | 0985364 A3 | 3/2000 |
| EP | 0985364 B1 | 3/2000 |
| FR | 2813777 | 3/2002 |
| FR | 2848535 | 6/2004 |
| GB | 491053 | 8/1938 |
| GB | 2099305 A | 12/1982 |
| GB | 2227938 A | 8/1990 |
| GB | 1046146 | 10/1996 |
| WO | WO 8707122 | 12/1987 |
| WO | WO 9203947 | 3/1992 |
| WO | WO 9531154 | 11/1995 |
| WO | WO 99/55271 | 11/1999 |
| WO | 0064324 | 11/2000 |
| WO | 2005110183 | 11/2005 |
| WO | 2006071300 | 7/2006 |

OTHER PUBLICATIONS

Medical Textiles, Nov. 1999 "Crimped Bristle Toothbrush". "Nonwoven Removes Stains", "Dental Floss".
Tetra Medical Supply Corp.; Product Information; Jan. 4, 2000; www.tetramed.com/dress.htm.
Spandage; Product Information; Jan. 4, 2000; spandage.com/main.htm.
FootSmark Products; Product Information-Toe Caps & DigiCushions; Jan. 4, 2000; www.footsmart.com.
Abstract of Japanese Patent No. JP06205723.
Abstract of Japanese Patent No. JP06285108.
Abstract of Japanese Patent No. JP10243818.
Abstract of Japanese Patent No. JP05044165.
PCT Search Report—Nov. 6, 2006.

* cited by examiner

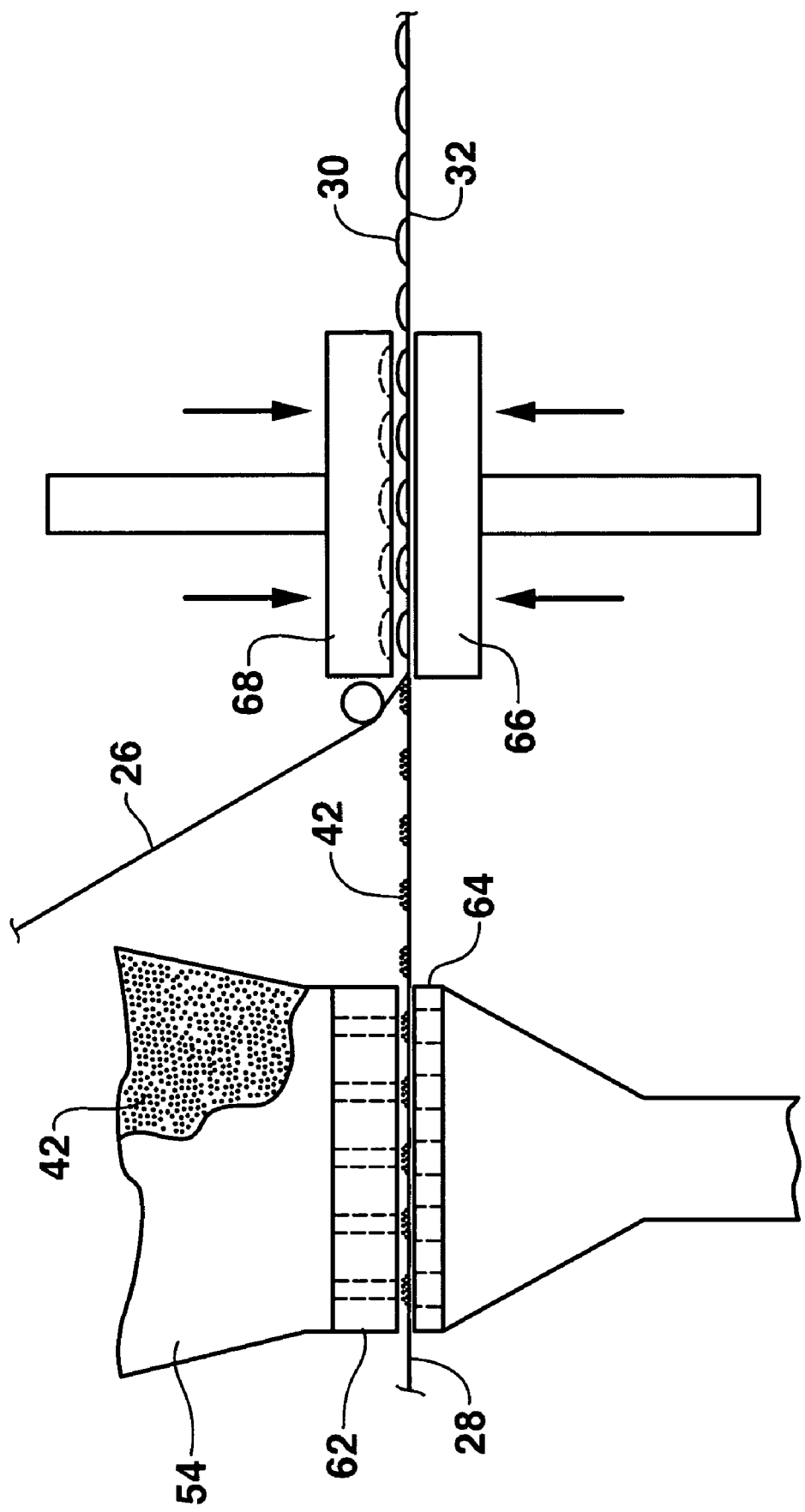

APPLICATOR WITH DISCRETE POCKETS OF A COMPOSITION TO BE DELIVERED WITH USE OF THE APPLICATOR

BACKGROUND OF THE INVENTION

Finger wipes or covers are known and used in the art for a variety of purposes. A common use of finger wipes (also know as a "finger glove" in the art) is for applying ointments, medications, alcohol, oral anesthetics, and the like, to various body parts. Such devices may also be utilized to remove various substances, such as makeup, or to clean body parts or other objects.

Finger wipes have proven particularly useful in the field of dental hygiene in that they provide a portable and efficient means for more frequent dental care, and as a cleaning device that can be easily used in public. In particular, a number of finger-mounted teeth cleaning devices have been developed that can be placed over a finger and wiped over the user's teeth and gums. These devices are typically small, portable, and disposable.

Examples of oral cleaning devices and finger wipes are disclosed, for instance, in U.S. Pat. No. 6,721,987 to McDevitt. et al. and in U.S. Pat. No. 6,647,549 also to McDevitt, et al., which are incorporated herein by reference. An oral hygiene finger device is also described in U.S. Pat. No. 5,445,825 to Copelan et al. Other finger-mounted teeth cleaning devices were developed to contain an elastomeric material to help prevent the device from slipping or falling off the user's finger during cleaning. Examples of such teeth cleaning devices are disclosed in U.S. Pat. Nos. 5,068,941 to Dunn; U.S. Pat. No. 5,348,153 to Cole; U.S. Pat. No. 5,524,764 to Kaufman et al.; and PCT Publication No. WO 95/31154 to Mittiga et al.

Finger wipes that incorporate an integral additive or composition, such as an oral hygiene agent, are a convenient and desirable product. However, it may be difficult to incorporate an adequate supply of the desired composition with certain conventional finger wipe constructions, or to adequately preserve or protect the additive prior to use. For example, the use of an aqueous adhesive composition to apply the additive directly to the wipe can be problematic for certain types of additives, particularly certain types of soluble compositions, such as encapsulated compositions, including flavoring oils and the like. These encapsulated additives are intended to be activated by the user's saliva or water upon use, but can prematurely interact with the aqueous adhesive during initial application, thus resulting in an overall decrease in the effectiveness of the additive.

It is also a desirable feature of conventional finger wipes to incorporate a textured outer surface to enhance the cleaning or scrubbing effect of the wipes. For example, conventional wipes may include an outer nonwoven material layer that has been thermally bonded in a pattern so as to produce protruding unbonded regions, sometimes referred to in the art as "point unbonded" (PUB) material. These materials serve a useful purpose, but increase the difficulty and complexity of incorporating desired additives to the wipe.

Thus, a need exists in the art for improved ways to incorporate additives with a wipe, particularly for wipes incorporating water soluble additives.

DEFINITIONS

As used herein, the term "breathable" means pervious to water vapor and gases. In other words, "breathable barriers" and "breathable films" allow water vapor to pass therethrough, but are substantially impervious to liquid water. For example, "breathable" can refer to a film or laminate having water vapor transmission rate (WVTR) of at least about 300 $g/m^2/24$ hours measured using ASTM Standard E96-80, upright cup method, with minor variations as described in the following Test Procedure.

A measure of the breathability of a fabric is the water vapor transmission rate (WVTR) which, for sample materials, is calculated essentially in accordance with ASTM Standard E96-80 with minor variations in test procedure as set forth in detail in the '549 patent incorporated herein by reference.

As used herein, the terms "elastic" and "elastomeric" are generally used to refer to materials that, upon application of a force, are stretchable to an elongated length, and which will retract at least about 50% of its elongation upon release of the stretching, biasing force.

As used herein, "meltblown fibers" refers to fibers formed by extruding a molten thermoplastic material through a plurality of fine, usually circular, die capillaries as molten threads or filaments into converging high velocity, usually hot, gas (e.g. air) streams which attenuate the filaments of thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin. et al. Meltblown fibers are microfibers which may be continuous or discontinuous, are generally smaller than 10 microns in average diameter, and are generally tacky when deposited on a collecting surface.

As used herein, a "liquid impermeable layer" refers to any material that is relatively impermeable to the transmission of fluids, i.e. a fabric having a liquid impermeable layer can have a liquid strikethrough ratio of 1.0 or less according to ASTM test method 22.

As used herein, the term "neck-bonded" refers to an elastic member being bonded to a non-elastic member while the non-elastic member is extended in the machine direction creating a necked material. "Neck-bonded laminate" refers to a composite material having at least two layers in which one layer is a necked, non-elastic layer and the other layer is an elastic layer thereby creating a material that is elastic in the cross direction. Examples of neck-bonded laminates are such as those described in U.S. Pat. Nos. 5,226,992; 4,981,747; 4,965,122; and 5,336,545, all to Morman, all of which are incorporated herein by reference thereto.

As used herein, "spunbond fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. Nos. 4,340,563 to Appel, et al.; U.S. Pat. No. 3,692,618 to Dorschner. et al.: U.S. Pat. No. 3,802,817 to Matsuki, et al.; U.S. Pat. No. 3,338,992 to Kinney; U.S. Pat. No. 3,341,394 to Kinney; U.S. Pat. No. 3,502,763 to Hartman; and U.S. Pat. No. 3,542,615 to Dobo. et al. Spunbond fibers are generally not tacky when they are deposited on a collecting surface. Spunbond fibers are generally continuous and have average diameters (from a sample of at least 10) larger than 7 microns, and more particularly, between about 10 and 40 microns.

As used herein, the term "stretch-bonded" refers to a composite material having at least two layers in which one layer is a gatherable layer and the other layer is an elastic layer. The layers are joined together when the elastic layer is in an extended condition so that upon relaxing the layers, the gatherable layer is gathered. For example, one elastic member can be bonded to another member while the elastic member is extended at least about 25 percent of its relaxed length. Such a multilayer composite elastic material may be stretched until the nonelastic layer is fully extended. One type of stretch-bonded laminate is disclosed, for example, in U.S. Pat. No. 4,720,415 to Vander Wielen, et al., which is incorporated herein by reference. Other composite elastic materials are described and disclosed in U.S. Pat. Nos. 4,789,699 to Kieffer, et al.; U.S. Pat. No. 4,781,966 to Taylor; U.S. Pat. No. 4,657,802 to Morman; and U.S. Pat. No. 4,655,760 to Morman, et al., all of which are incorporated herein by reference thereto.

As used herein, the term "texturized" refers to a base web having projections from a surface of the web in the Z-direction. The projections can have a length, for instance, from about 0.1 mm to about 25 mm, particularly from about 0.1 mm to about 5 mm, and more particularly from about 0.1 mm to about 3 mm. The projections can take on many forms and can be, for instance, bristles, tufts, loop structures such as the loops used in hook and loop attachment structures, and the like.

SUMMARY

Objects and advantages of the invention will be set forth below in the following description, or may be obvious from the description, or may be learned through practice of the invention.

The present disclosure is directed generally to applicators used to deliver an internally stored composition upon use of the device, and encompasses any manner of cleaning mitt, pad, or like structure incorporating the novel aspects of the invention. For ease of description only, aspects of the invention are explained herein by reference to finger wipe embodiments, particularly dental finger wipes. However, it should be appreciated that the invention is not limited to such devices.

In certain embodiments, the applicator is a disposable tubular or mitt structure designed to fit onto the finger(s) or hand of a user. In a particular embodiment, the applicator is configured as a finger wipe designed for cleaning the teeth or gums of a person or animal with an oral hygiene composition carried by the wipe. Further, the dental wipe is particularly well suited for use by small children learning how to clean their teeth.

The applicator of the present invention can also be used in other applications. For instance, a finger wipe embodiment may be used to clean or treat other parts of the body such as the eyes, the ears, the nose, and the like. The finger wipe may be used to apply a medicine, lotion, ointment, cleaning agent, or the like to any part of the body, or any other object.

In still other embodiments, the applicator can be used to clean various utensils, objects or surfaces and/or to polish various items with any number of compositions or agents carried by the wipe. For example, in one embodiment, a finger wipe can be used to polish silver with a polish carried by the wipe.

For the finger wipe embodiments, the tubular structure has an open end for insertion of one or more of a user's fingers. The tubular structure is formed from a front panel, and an opposite back panel. The front panel is configured to perform a desired function with the wipe, such as cleaning, scrubbing, polishing, application of a composition, and so forth. The front panel can include a liquid impermeable material disposed to prevent liquids from contacting the user's fingers during use of the applicator, and an outer liquid permeable cover material. A plurality of discrete pockets are formed between the cover material and the liquid impermeable material. Any desired composition is contained within each of the pockets and is delivered with use of the applicator by migrating through the permeable cover material.

It should be appreciated that the invention is not limited to any particular type of composition contained within the pockets. In a particular embodiment, the composition is soluble and activated by water or the user's saliva, and remains protected in the pockets until use. The composition may be any oral hygiene agent. For example, the composition may be an encapsulated agent, such as an encapsulated flavoring oil, that is released when the capsules dissolve in an aqueous medium. The composition may be a soluble powder or granular substance, such as a cleaning agent. In a particular embodiment, the composition may be an effervescing particulate flavoring material that creates a distinct flavor and effervesces upon activation. Particularly for children, this type of agent emits a gratifying audible sound and a tingling sensation in the mouth. In general, the composition may be any desired substance that, upon mixing with an aqueous medium when using the wipe, migrates through the cover material to perform its intended function.

Various materials may be used in construction of the panel members, and at least one of the panels may be formed of an elastomeric material to provide the wipe with form-fitting properties. The panel members can be the same or a different material, depending on the desired characteristics of the applicator. In one embodiment, the application panel and back panel are formed separately and subsequently attached along a seam around the closed periphery portion of the wipe to define the elongated closed-end tubular structure having a finger insertion opening at one end.

In a particular embodiment, the application panel includes a thermoplastic nonwoven cover material that is thermally fused to the liquid impermeable material, such as a thermoplastic film, fibrous material, laminate, and the like, at distinct fused portions. Unfused portions between the cover material and the liquid impermeable material define the discrete pockets. The composition is deposited between the materials prior to fusing in a pattern that corresponds to the unfused portions. The composition can be initially deposited onto the liquid impermeable material utilizing any suitable deposition technique, such as template, vacuum plate, adhesive, textured substrates, electrostatic, xerographic, printing (e.g., gravure), patterned transfer roll (vacuum or adhesive), and the like.

The pockets may have any desired geometry and size. In a particular embodiment, the pockets are generally circular in cross section and have a diameter of generally between about 2 mm to about 10 mm. In an alternate embodiment, the pockets have an elongated shape. The pockets have a height dimension in the Z direction with respect to a surface plane of the fused portions, and may have a width to height ratio of generally between about 1 to about 5. The pockets may serve the additional function of enhancing the surface scrubbing and cleaning effect of the cover material, and may have a size, texture, and flexibility selected for this purpose.

The pockets may be defined in any desired pattern on the cover material. In one embodiment, the pockets are defined in a generally uniform pattern over the surface of the cover material. In another embodiment, the pockets are defined in a discrete zone generally closer to the closed end of the tubular structure, which is the location generally applied by the user to an object. This embodiment minimizes waste of the composition. With this embodiment, other surface area regions of the cover material may include additional textured features to enhance the scrubbing or cleaning effect of the wipe. In this regard, the cover material may be formed from a nonwoven material layer that has been texturized by any one of a number of conventional processes. The textured features may be pockets between the material layers that are not filled with the composition, but are formed in the same process.

In addition to the composition contained within the pockets, various other additives can also be applied, if desired, to the finger wipe during manufacturing and/or by the consumer. For example, cationic materials, such as chitosan (poly-N-acetylglucosamine), chitosan salts, cationic starches, etc., can be applied to a wipe of the present invention to help attract negatively charged bacteria and deleterious acidic byproducts that accumulate in plaque. Examples of other suitable additives include, but are not limited to, dental agents, such as fluorides, peppermint oil, mint oil and alcohol mixtures; flavoring agents, such as xylitol; anti-microbial agents; polishing agents; hemostatic agents; surfactants; anti-ulcer components; and the like.

Additives can be applied to the cover material in the form of an aqueous solution, non-aqueous solution (e.g., oil), lotions, creams, suspensions, gels, etc. When utilized, the aqueous solution may be coated, saturated, sprayed, or impregnated into the material. In some embodiments, the additives can be applied asymmetrically. Moreover, in some instances, it may be desired that the additives comprise less than about 100% by weight of the wipe, and in some embodiments, less than about 50% by weight of the wipe, and particularly less than 10% by weight of the wipe.

It should be noted that any given range presented herein is intended to include any and all lesser included ranges. For example, a range of from 45-90 would also include 50-90; 45-80; 46-89 and the like. Thus, the range of 95% to 99.999% also includes, for example, the ranges of 96% to 99.1%, 96.3% to 99.7%, and 99.91 to 99.999%.

Various features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth in the specification, which makes reference to the appended drawings, in which:

FIG. 8 is a simplified view of an alternate production process for making components of wipes according to the invention.

Figure 1:
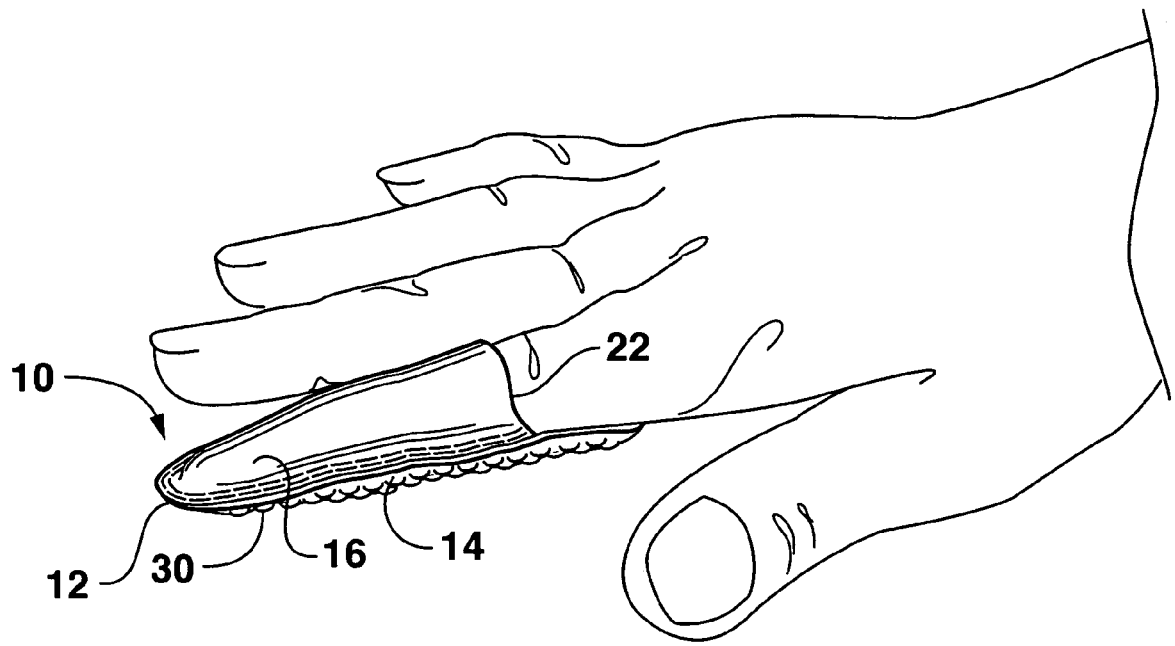
FIG. 1 is a perspective view of an applicator according to the invention configured as a finger wipe fitted onto a user's finger.

Repeat use of reference characters in the present specification and drawings is intended to represent the same or analogous features or elements of the invention.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used with another embodiment to yield a still further embodiment. Thus, it is intended that the present invention covers such modifications and variations as come within the scope of the appended claims and their equivalents.

Embodiments of an applicator according to the invention are illustrated in the figures as a finger wipe 10 in the shape of a tubular structure 12, in particular a finger wipe intended to be placed over one or more of a user's fingers for use as a cleaning or polishing device, or any other use. In the illustrated embodiments, the finger wipe 10 is made from a front application panel 14, and a back panel 16. The panels 14, 16 may be sections of the same or a different material, and are bonded or attached together along an edge seam 18 in a finger-shaped pattern so that the bonded sections form the closed end tubular structure 12 with an opening 22 for the insertion of a user's finger(s) into the space 24 between the panels 14, 16. The panels may be bonded or attached by any conventional means, including thermal or ultrasonic bonding of point bonds 20 around the edge seam 18. The panels 14, 16 may be bonded or otherwise attached along the seam 18 in generally continuous pieces of materials, wherein the materials are subsequently cut adjacent to the seams 18 such that the finger wipe 10 is formed. In an alternative embodiment, the panels 14, 16 are cut and bonded in a single processing step.

Figure 2:
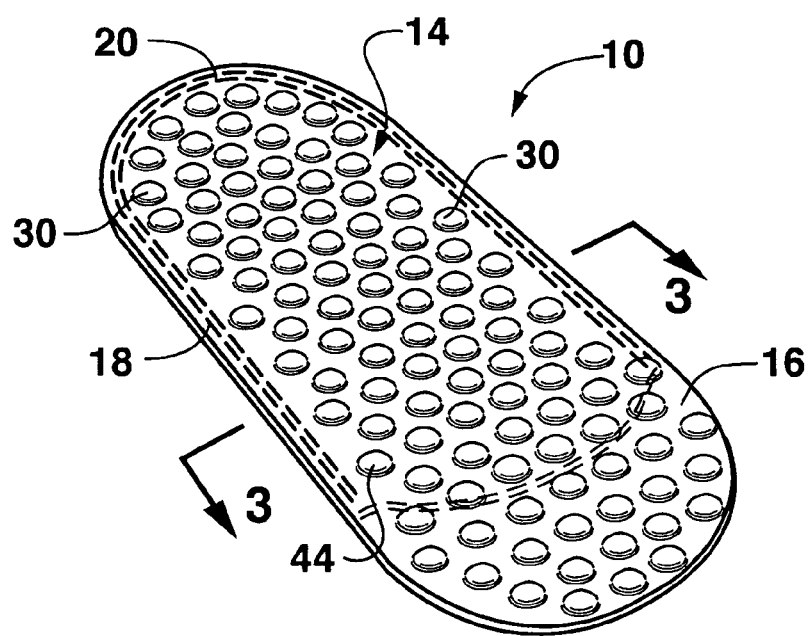
FIG. 2 is a perspective view of the front panel side of the finger wipe shown in FIG. 1.
Figure 3:
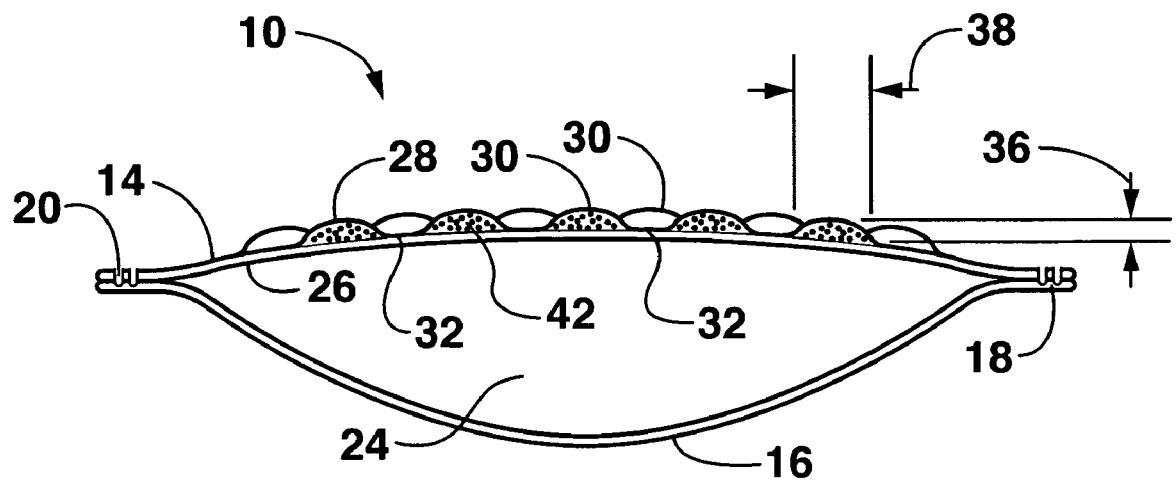
FIG. 3 is a cross sectional view of the finger wipe shown in FIG. 1 taken along the lines indicated.

It may be desired that one or both of the panels 14, 16 include a textured outer surface, such as the surface illustrated in FIG. 2. A well known method for forming a textured surface in a nonwoven material is a thermal bonding process wherein raised unbonded (or lightly bonded) areas are surrounded by bonded regions. A textured material formed by such a process may be desired as an outer cover layer 28 (FIG. 3) in finger wipes 10 according to the invention, as illustrated generally in the figures by raised "bumps" or "tufts" 44 on the surface cover layer 28.

Referring to FIGS. 1 and 2, the panel 14 may have a length greater than the opposite panel 16 such that a longitudinally extending portion of the panel section 14 extends beyond the edge of the section 16 and serves as a "pull-on" tab to facilitate placement of the finger wipe 10 over the user's finger. It should be appreciated that a pull-on tab or section may be positioned on any suitable portion of the finger wipe 10.

Figure 5:
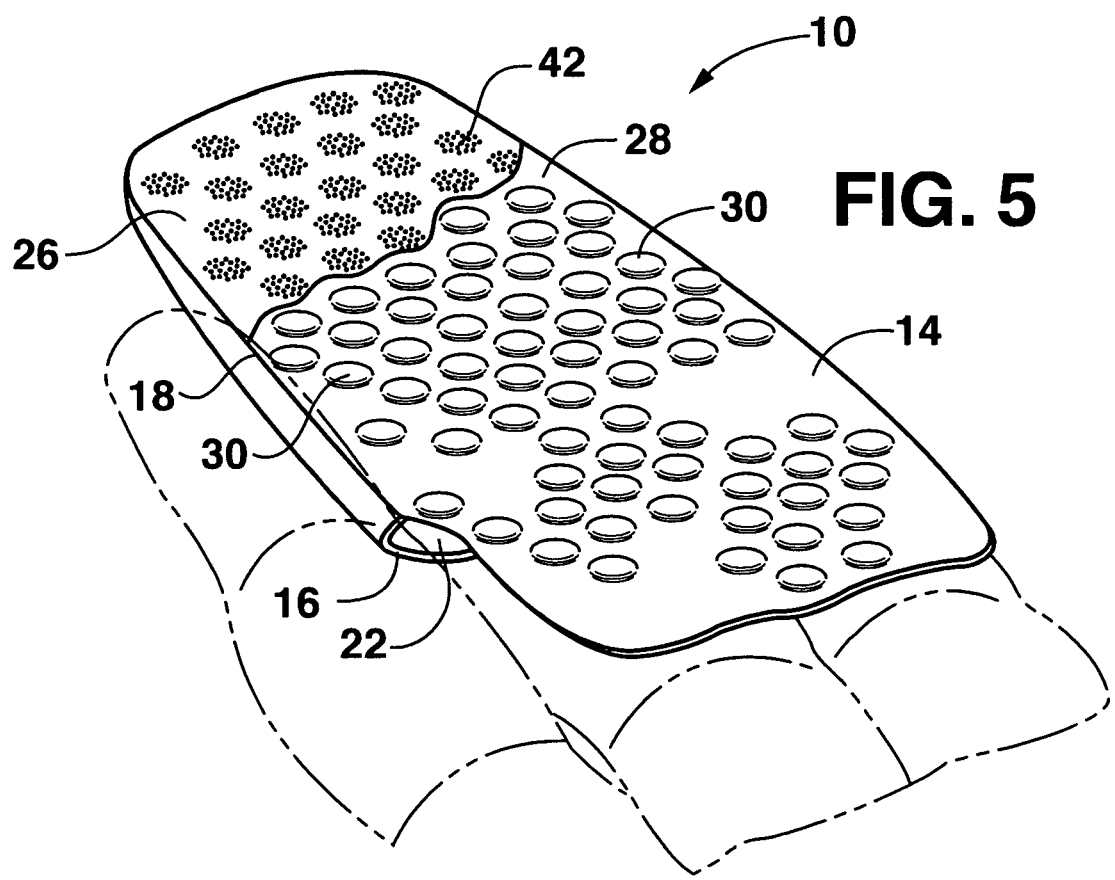
FIG. 5 is a perspective and partial cut-away view of an embodiment of a two-finger wipe according to aspects of the invention.
Figure 6:
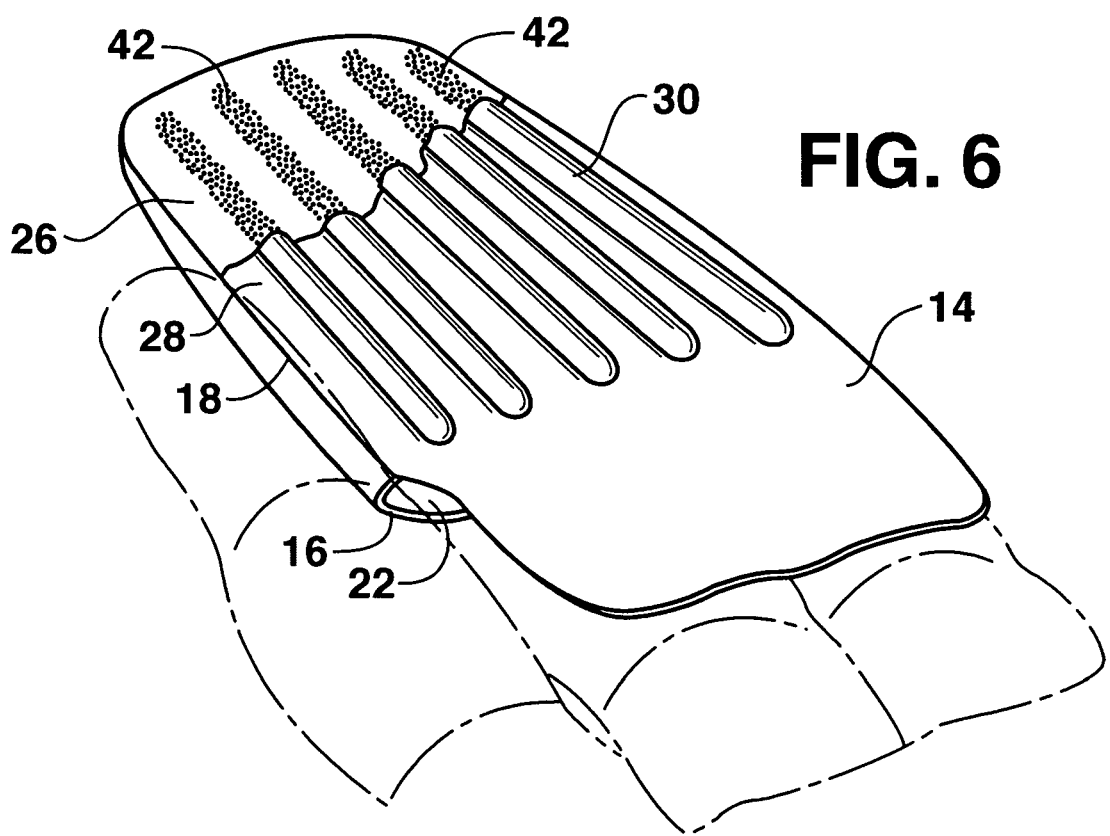
FIG. 6 is a perspective and partial cut-away view of an alternative two-finger wipe according to aspects of the invention.

The dimensions of finger wipes 10 will depend upon the particular application and purpose for which the finger wipe is to be used. For instance, the finger wipe can be constructed in order to fit around the finger of an adult or the finger of a child, as illustrated in FIG. 1. Further, the finger wipe can also be constructed to fit around two or more fingers, as seen in FIGS. 5 and 6. For most single finger wipes, the wipe should have a length of from about 1 inch to about 7 inches and a median flattened width of from about 0.5 inches to about 4 inches. When constructed to fit around two fingers, the finger wipe can have a median width of from about 0.75 inches to about 2.5 inches, depending on the elasticity of the wipe.

In general, the finger wipes 10 of the present invention can be formed from a variety of materials. U.S. Pat. No. 6,647,549 incorporated herein by reference describes various suitable materials, and combinations of materials, that may be used for wipes 10 incorporating the unique seam structure of the present invention. Non-limiting examples of suitable materials are described in greater detail below.

Referring to the figures in general, the front panel 14 of the wipe embodiments 10 is configured to perform a desired function with the wipe, such as cleaning, scrubbing, polishing, application of a composition, and so forth. The front panel 14 includes a liquid impermeable material 26, such as a breathable film, disposed to prevent liquids from contacting the user's fingers during use of the wipe 10. The front panel 14 includes an outer liquid permeable cover material 28, such as a thermoplastic nonwoven material.

A plurality of discrete pockets 30 are formed between the cover material 28 and liquid impermeable material 26. Any desired composition 42 is contained within each of the discrete pockets 30. The composition 42 migrates through the cover material 28 upon being wetted with use of the finger wipe 10.

It should be appreciated that the invention is not limited to any particular type of composition 42 contained within the pockets 30. In a particular embodiment, the composition 42 is soluble and activated by water or the user's saliva. Prior to use of the wipe 10, the composition 42 remains essentially protected within the pockets 30. In a particular embodiment, the composition 42 may be an oral hygiene agent, particularly an encapsulated agent such as a flavoring oil that is released when the capsules dissolve in an aqueous medium, such as a user's saliva. The composition 42 may be a soluble powder or granular substance, such as a cleaning agent. In another embodiment, the composition 42 may be an effervescing particulate flavoring material that creates a distinct flavor and also effervesces upon activation. It should thus be appreciated that the composition 42 may be any desired substance that, upon mixing with an aqueous medium when using the wipe, migrates through the cover material 28 to perform its intended function.

With certain embodiments, the front panel 14 may be formed from a thermoplastic nonwoven cover material 28 that is thermally fused to the liquid impermeable barrier material 26. The barrier material 26 may be a thermoplastic film, fibrous material, laminate, and the like. The two materials are fused together in a pattern that defines fused portions 32 and unfused portions. The unfused portions define the discrete pockets 30 in which the composition 42 is contained. The composition 42 is deposited between the materials prior to the fusing process in a pattern that corresponds to the unfused portions. The composition 42 can be initially deposited onto either of the layers 26, 28 utilizing any suitable deposition technique, such as a template, vacuum plate, adhesive, electrostatic deposition, printing techniques, patterned transfer rolls, and the like. Exemplary processes will be described below with reference to FIGS. 6 and 7.

It should be appreciated that the pockets 30 may have any desired geometry and size. For example, in the embodiments of FIGS. 2 and 5, the pockets 30 are generally circular in cross section and may have a diameter 38 of between about 2 mm to about 10 mm. In an alternative embodiment illustrated in FIG. 6, the pockets 30 have an elongated shape and appear as ribs on the surface of the wipe 10. The pockets 30 have a height dimension 36 (FIG. 3) in the Z direction with respect to a surface plane of the fused portions 32. The pockets 30 may have a width-to-height ratio generally between about 1 to about 5.

The pockets 30 may serve the additional function of a textured surface that enhances the surface scrubbing and cleaning effect of the cover material 28 and, thus, may have a size, texture, and flexibility selected for this purpose.

Figure 4:
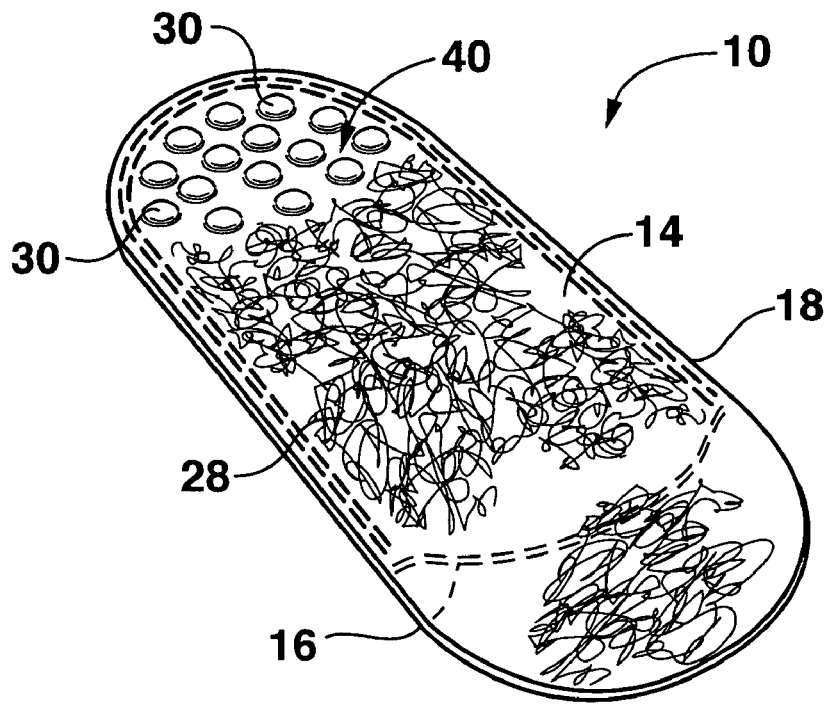
FIG. 4 is a perspective view of an alternate embodiment of a finger wipe according to the invention.

It should also be appreciated that the pockets 30 may be defined in any desired pattern over the surface area of the cover material 28. For example, in the embodiment of FIG. 2, the pockets 30 are defined in a generally uniform pattern over the surface of the cover material 28. In an alternate embodiment illustrated for example in FIG. 4, the pockets 30 are defined in a discrete zone 40 that may be closer to the closed end of the tubular structure 12 where the composition within the pockets 30 may be readily applied to a surface by the user's fingers. It should be appreciated that the discrete zones 40 may be defined at any location on the surface area of the cover material 28.

In any zone of the cover material 28 that does not include the pockets 30, it may be desired that the cover material 28 include additional textured surface features to enhance the cleaning or scrubbing effect of the material 28. In this regard, the cover material may be formed from a nonwoven material layer that has been texturized by any one of a number of conventional processes, as discussed in greater detail below. The textured features may be defined by additional pockets between the material layers 26, 28 that are not filled with the composition 42 during the manufacturing process, but are formed in the same process.

In addition to the composition 42 carried within the discrete pockets 30, various other additives can be applied to the cover material 28. Suitable additives can be applied to the tubular structure material in the form of an aqueous solution, non-aqueous solution, lotion, cream, suspensions, gels, etc. Examples of suitable additives include dental agents, such as fluorides, peppermint oil, mint oil, and alcohol mixtures; flavoring agents; anti-microbial agents; polishing agents; hemostatic agents; surfactants; anti-ulcer components; and so forth. Various non-limiting examples of additional additives are described in greater detail below.

It may be desired that the tubular structure of the wipe 10 have elastomeric form-fitting properties. In this regard, either or both of the panels 14, 16 may be formed of a suitable elastomeric material, examples of such materials are discussed below.

Figure 7:
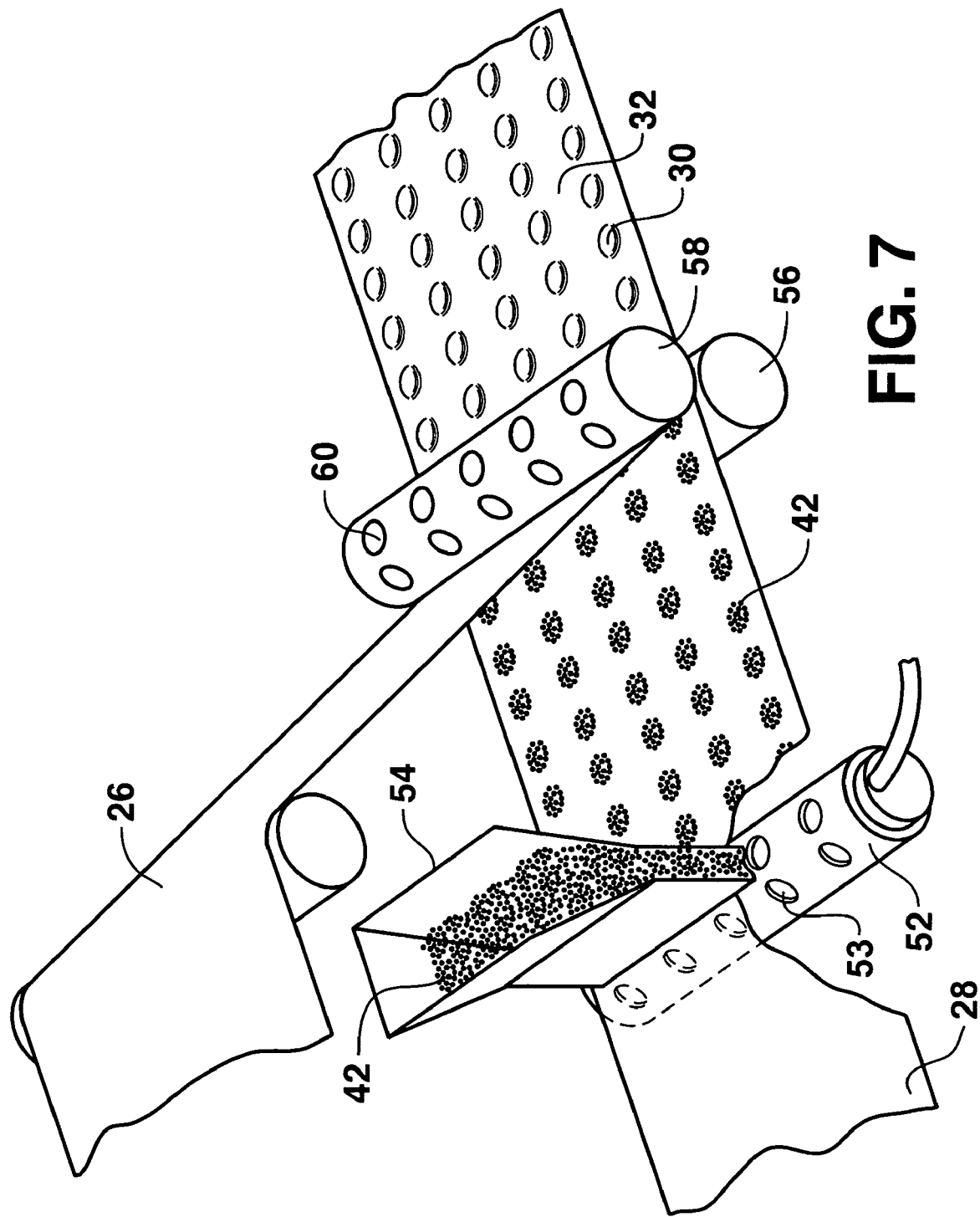
FIG. 7 is a simplified view of a production process that may be used for making components used in wipes according to the invention.

FIG. 7 is a simplified diagrammatic view of a process for defining the discrete pockets 30 containing the composition 42. In this process, the permeable cover layer material 28 is conveyed over a vacuum roll 52 having a pattern of holes 53 defined therethrough. A hopper 54 containing the composition 42 deposits the composition onto the cover material 28 and the suction roll 52 defines discrete deposits of the composition 42 in a pattern corresponding to the holes in the roll 52. The barrier material 26 is then introduced into the process between a patterned bonding roll 58 and a smooth bonding roll 56. The patterned roll 58 includes a pattern of recesses or holes 60 corresponding to the deposition pattern of the deposits 42. Thus, as the materials 26 and 28 pass through the nip between the bonding rolls 56, 58, the cover material 28 is thermally fused to the barrier material 26 in fused regions 32. Unfused regions result from the recesses 60 in the patterned bonding roll, with the unfused portions defining the cover of the discrete pockets 30.

FIG. 8 illustrates another simplified exemplary process for forming the discrete pockets in the front panel 14. In this embodiment, a hopper 54 containing the composition 42 is disposed over a patterned distribution plate 62 that is used to deliver discrete deposits of the composition 42 onto the cover material 28. A patterned suction plate 64 is disposed under the material 28 for forming the discrete deposits of the composition 42 in the desired pattern. The barrier material 26 is then introduced into the process between a patterned bonding plate 68 and an unpatterned plate 66. These plates are used to fuse the materials together such that fused portions 32 are defined and unfused portions create the cover for the discrete pockets 30.

Various non-limiting examples of materials that may be used in construction of finger wipes 10 according to the invention are discussed below.

As mentioned, the panels 14,16 are formed from a base web that may include one or more layers of fibrous materials used in the art for making wipes. For example, either or both of the panel sections may comprise a liquid absorbent material or a non-absorbent material. When comprising a liquid absorbent material, the base webs may comprise any suitable fabric material, such as a woven fabric, a nonwoven fabric, or a knitted fabric.

In one embodiment, the base web comprises a spunbond web, a coform web, a tissue web, a meltblown web, a bonded carded web, and laminates thereof. A nonwoven material can be made from various fibers, such as synthetic or natural fibers. For instance, in one embodiment, synthetic fibers, such as fibers made from thermoplastic polymers, can be used to construct the cover layer of the present invention. For example, suitable fibers could include melt-spun filaments, staple fibers, melt-spun multi-component filaments, and the like. These synthetic fibers or filaments used in making the nonwoven material may have any suitable morphology and may include hollow or solid, straight or crimped, single component, conjugate or biconstituent fibers or filaments, and blends or mixtures of such fibers and/or filaments, as are well known in the art.

The synthetic fibers used in the present invention may be formed from a variety of thermoplastic polymers where the term "thermoplastic polymer" refers to a long chain polymer that repeatedly softens when exposed to heat and substantially returns to its original state when cooled to ambient temperature. As used herein, the term "polymer" generally includes, but is not limited to, homopolymers, copolymers, such as for example, block, graft, random, and alternating copolymers, terpolymers, etc., and blends and modifications thereof.

Exemplary thermoplastics include, without limitation, poly(vinyl) chlorides, polyesters, polyamides, polyfluorocarbons, polyolefins, polyurethanes, polystyrenes, poly(vinyl) alcohols, caprolactams, and copolymers of the foregoing, and elastomeric polymers such as elastic polyolefins, copolyether esters, polyamide polyether block copolymers, ethylene vinyl acetates (EVA), block copolymers having the general formula A-B-A' or A-B like copoly(styrene/ethylene-butylene), styrene-poly(ethylene-propylene)-styrene, styrene-poly(ethylene-butylene)-styrene, (polystyrene/poly(ethylene-butylene)/polystyrene, poly(styrene/ethylene-butylene/styrene), A-B-A-B tetrablock copolymers and the like.

Many polyolefins are available for fiber production, for example polyethylenes such as Dow Chemical's PE XU 61800.41 linear low-density polyethylene ("LLDPE") and 25355 and 12350 high-density polyethylene ("HDPE") are such suitable polymers. Fiber-forming polypropylenes include Exxon Chemical Company's Escorene® PD 3445 polypropylene and Montell Chemical Co.'s PF-304 and PF-015. Many other polyolefins are commercially available and include polybutylenes and others.

Synthetic fibers added to the nonwoven web can also include staple fibers that can be added to increase the strength, bulk, softness and smoothness of the base sheet. Staple fibers can include, for instance, various polyolefin fibers, polyester fibers, nylon fibers, polyvinyl acetate fibers, cotton fibers, rayon fibers, non-woody plant fibers, and mixtures thereof.

Besides, or in addition to, synthetic fibers, pulp fibers can also be used to construct the cover layer. The pulp fibers used in forming the cover layer may be soft wood fibers having an average fiber length of greater than 1 mm, and particularly from about 2 to 5 mm based on a length weighted average. Such fibers can include northern softwood kraft fibers, redwood fibers, and pine fibers. Secondary fibers obtained from recycled materials may also be used. In addition, hardwood pulp fibers, such as eucalyptus fibers, or thermomechanical pulp can also be utilized in the present invention.

In some embodiments of the present invention, the base web can include a hydraulically entangled web (or hydroentangled). Hydroentangled webs, which are also known as spunlace webs, refer to webs that have been subjected to columnar jets of a fluid that cause the fibers in the web to entangle. For example, in one embodiment, the cover layer can comprise HYDROKNIT®, a nonwoven composite fabric that contains 70% by weight pulp fibers that are hydroentangled into a continuous filament material. HYDROKNIT® material is commercially available from Kimberly-Clark Corporation of Roswell, Ga. Hydraulic entangling may be accomplished utilizing conventional hydraulic entangling equipment such as may be found in, for example, U.S. Pat. Nos. 3,485,706 to Evans or U.S. Pat. No. 5,389,202 to Everhart, et al., the disclosures of which are hereby incorporated by reference.

In one embodiment, the base web may comprise a laminate containing two or more webs. For instance, the web may comprise a spunbonded/meltblown/spunbonded laminate, a spunbonded/meltblown laminate and the like.

For nonwoven webs containing substantial amounts of synthetic fibers, the webs may be bonded or otherwise consolidated in order to improve the strength of the web. Various methods may be utilized in bonding webs of the present invention. Such methods include through air bonding and thermal point bonding as described in U.S. Pat. No. 3,855,046 to Hansen, et al. which is incorporated herein by reference. In addition, other conventional means of bonding, such as oven bonding, ultrasonic bonding, hydroentangling, or combinations of such techniques, may be utilized in certain instances.

In one embodiment, thermal point bonding is used which bonds the fibers together according to a pattern. In general, the bonding areas for thermal point bonding, whether pattern unbonded or pattern bonded fabrics, can be in the range of 50% total bond area or less. More specifically, the bond areas of the present inventive webs can be in the range of from about 60% to about 10% total bond area.

When the finger wipe of the present invention is used to scrub adjacent surfaces or is to be used in dental applications, in some embodiments, the cover layer 28 may include a texturized surface, such as the surface illustrated in the embodiments shown in FIGS. 2 and 5. When used in dental applications, for instance, the texturized surface can facilitate removal of residue and film from the teeth and gums.

The manner in which a texturized surface is formed on a nonwoven web for use in the present invention can vary depending upon the particular application of the desired result. The panel sections may be made from a nonwoven web that has been thermally point unbonded to form a plurality of tufts 44. As used herein, a substrate that has been "thermally point unbonded" refers to a substrate that includes raised unbonded areas or lightly bonded areas that are surrounded by bonded regions. For example, as shown in the figures, bumps or tufts are the unbonded or lightly bonded areas that form raised projections off the surface of the nonwoven web to provide the necessary texture.

The material used for the point unbonding process can vary depending upon the particular application. For instance, the material can be a single layer or can include multiple layers of material. For most applications, the total basis weight of the material should be at least 1 osy, and particularly from about 3 osy to about 9 osy. Higher basis weights are needed in order to produce tufts with an appropriate height.

Besides point unbonded materials, there are many other methods for creating texturized surfaces on base webs and many other texturized materials can be utilized.

Examples of known nonwoven, texturized materials, include rush transfer materials, flocked materials, wire-formed nonwovens, and the like. Moreover, through-air bonded fibers, such as through-air bonded bicomponent spunbond, or point unbonded materials, such as point unbonded spunbond fibers, can be incorporated into the base web to provide texture to the wipe.

Textured webs having projections from about 0.1 mm to about 25 mm, such as pinform meltblown or wireform meltblown, can also be utilized in a base web of the present invention. Still another example of suitable materials for a texturized base web includes textured coform materials. In general, "coform" means a process in which at least one meltblown diehead is arranged near a chute through which other materials are added to the web while it forms. Such other materials can include, for example, pulp, superabsorbent particles, or cellulose or staple fibers. Coform processes are described in U.S. Pat. Nos. 4,818,464 to Lau and U.S. Pat. No. 4,100,324 to Anderson. et al. Webs produced by the coform process are generally referred to as coform materials.

In one embodiment, the texturized material can be a loop material. As used herein, a loop material refers to a material that has a surface that is at least partially covered by looped bristles that can vary in height and stiffness depending upon the particular application. Further, the looped bristles can be sparsely spaced apart or can be densely packed together. The loop material can be made in a number of different ways. For example, the loop can be a woven fabric or a knitted fabric. In one embodiment, the loop material is made by needle punching loops into a substrate. In other embodiments, the loop material can be formed through a hydroentangling process or can be molded, such as through an injection molding process. Of course, any other suitable technique known in the art for producing looped bristles can also be used.

In one particular embodiment of the present invention, the loop material used in the finger wipe is a loop material commonly used in hook and loop fasteners. For example, VELCRO loops No. 002 made by VELCRO, USA, Inc. can be used. This material is made with nylon loops. In an alternative embodiment, the looped fastener material can be elastic. Elastic woven loop materials include VELSTRETCH Tape 9999 and MEDFLEX Tape 9399, both marketed by VELCRO, USA, Inc.

The liquid impermeable layer 26 may be separate a single material, or constitute a component of a base web. The liquid impermeable layer(s) can be made from liquid-impermeable plastic films, such as polyethylene and polypropylene films. Generally, such plastic films are impermeable to gases and water vapor, as well as liquids.

While completely liquid-impermeable films can prevent the migration of liquid from outside the wipe to the finger, the use of such liquid- and vapor-impermeable barriers can sometimes result in a relatively uncomfortable level of humidity being maintained in the finger wipe. As such, in some embodiments, breathable, liquid-impermeable barriers are desired. As used herein, the term "breathable" means that the barrier or film is pervious to water vapor and gases. In other words, "breathable barriers" and "breathable films" allow water vapor and gases to pass therethrough, but not necessarily liquids.

For instance some suitable breathable, liquid-impermeable barriers can include barriers such as disclosed in U.S. Pat. No. 4,828,556 to Braun, et al., which is incorporated herein in its entirety by reference. The breathable barrier of Braun, et al. is a multilayered, clothlike barrier comprised of at least three layers. The first layer is a porous nonwoven web; the second layer, which is joined to one side of the first layer, comprises a continuous film of PVOH; and the third layer, which is joined to either the second layer or the other side of the first layer not joined with the second layer, comprises another porous nonwoven web. The second layer continuous film of PVOH is not microporous, meaning that it is substantially free of voids that connect the upper and lower surfaces of the film.

In other cases, various films can be constructed with micropores therein to provide breathability. The micropores form what is often referred to as tortuous pathways through the film. Liquid contacting one side of the film does not have a direct passage through the film. Instead, a network of microporous channels in the film prevents water from passing, but allows water vapor to pass.

In some instances, the breathable, liquid-impermeable barriers are made from polymer films that contain any suitable substance, such as calcium carbonate. The films are made breathable by stretching the filled films to create the microporous passageways as the polymer breaks away from the calcium carbonate during stretching. In some embodiments, the breathable film layers can be used in thicknesses of from about 0.01 mils to about 5 mils, and in other embodiments, from about 0.01 mils to about 1.0 mils.

An example of a breathable, yet fluid penetration-resistant material is described in U.S. Pat. No. 5,591,510 to Junker, et al., which is incorporated herein by reference. The fabric material described in Junker, et al. contains a breathable outer layer of paper stock and a layer of breathable, fluid-resistant nonwoven material. The fabric also includes a thermoplastic film having a plurality of perforations which allow the film to be breathable while resisting direct flow of liquid therethrough.

In addition to the films mentioned above, various other breathable films can be utilized in the present invention. One type of film that may be used is a nonporous, continuous film, which, because of its molecular structure, is capable of forming a vapor-permeable barrier. Among the various polymeric films which fall into this type include films made from a sufficient amount of poly(vinyl alcohol), polyvinyl acetate, ethylene vinyl alcohol, polyurethane, ethylene methyl acrylate, and ethylene methyl acrylic acid to make them breathable. It is believed that films made from such polymers solubilize water molecules and allow transportation of those molecules from one surface of the film to the other. Accordingly, such films may be sufficiently continuous, i.e., nonporous, to make them liquid-impermeable but still allow for vapor permeability.

Still, other breathable, liquid-impermeable barriers that can be used in the present invention are disclosed in U.S. patent application Ser. No. 08/928,787 entitled "Breathable, Liquid-Impermeable, Apertured Film/Nonwoven Laminate and Process for Making the Same", which is incorporated herein in its entirety by reference. For example, breathable films and/or apertured films can be utilized in the present invention. Such films can be made within a laminate structure. In one embodiment, a breathable, liquid-impermeable, apertured film/nonwoven laminate material can be formed from a nonwoven layer, an apertured film layer, and a breathable film layer. The layers may be arranged so that the apertured film layer or the breathable film layer is attached to the nonwoven layer.

For instance, in one embodiment, an apertured film can be used in the present invention that is made from any thermoplastic film, including polyethylene, polypropylene, copolymers of polypropylene or polyethylene, or calcium carbonate-filled films. The particular aperturing techniques utilized to obtain the apertured film layer may be varied. The film may be formed as an apertured film or may be formed as a continuous, non-apertured film and then subjected to a mechanical aperturing process.

Liquid impermeable layers, as described above, can be used alone or incorporated into a laminate when used to construct various components of the finger wipe of the present invention. When incorporated into a laminate, the laminate can include various nonwoven webs in combination with the liquid impermeable layer. For instance, liquid impermeable laminates can be formed from many processes, such as, meltblowing processes, spunbonding processes, coforming processes, spunbonding/meltblowing/spunbonding processes (SMS), spunbonding/meltblowing processes (SM), and bonded carded web processes. For instance, in one embodiment, the nonwoven layer of a laminate liquid impermeable layer of the present invention is a spunbond/meltblown/spunbond (SMS) and/or spunbond/meltblown (SM) material. An SMS material is described in U.S. Pat. No. 4,041,203 to Brock. et al. which is incorporated herein in its entirety by reference. Other SMS products and processes are described for example in U.S. Pat. Nos. 5,464,688 to Timmons. et al., U.S. Pat. No. 5,169,706 to Collier, et al. and U.S. Pat. No. 4,766,029 to Brock, et al., all of which are also incorporated herein in their entireties by reference. Generally, an SMS material will contain a meltblown web sandwiched between two exterior spunbond webs. Such SMS laminates are available from Kimberly-Clark Corporation under marks such as Spunguard® and Evolution®. The spunbonded layers on the SMS laminates provide durability and the internal meltblown barrier layer provides porosity and additional clothlike feel. Similar to an SMS laminate, an SM laminate is a spunbond layer laminated to a meltblown layer.

In some embodiments, any of the above layers and/or materials can also be dyed or colored so as to form a base web or liquid impermeable layer having a particular color. For example, in one embodiment, the liquid impermeable layer can be provided with a colored background.

As described above, the finger wipes 10 may include one or more elastic components for providing the wipe with form-fitting properties. For example, one or both of the panel sections may be made of an elastic material, or include elastic components. The materials can contain elastic strands or sections uniformly or randomly distributed throughout the material. Alternatively, the elastic component can be an elastic film or an elastic nonwoven web.

In general, any material known in the art to possess elastomeric characteristics can be used in the present invention as an elastomeric component. Useful elastomeric materials can include, but are not limited to, films, foams, nonwoven materials, etc.

Other exemplary elastomeric materials which may be used include polyurethane elastomeric materials such as, for example, those available under the trademark ESTANE® from B.F. Goodrich & Co. or MORTHANE® from Morton Thiokol Corp., polyester elastomeric materials such as, for example, those available under the trade designation HYTREL® from E.I. DuPont De Nemours & Company, and those known as ARNITEL®, formerly available from Akzo Plastics of Amhem, Holland and now available from DSM of Sittard, Holland.

Another suitable material is a polyester block amide copolymer. Elastomeric polymers can also include copolymers of ethylene and at least one vinyl monomer such as, for example, vinyl acetates, unsaturated aliphatic monocarboxylic acids, and esters of such monocarboxylic acids. The elastomeric copolymers and formation of elastomeric nonwoven webs from those elastomeric copolymers are disclosed in, for example, U.S. Pat. No. 4,803,117.

When incorporating an elastomeric component, such as described above, into a base web of the present invention, it is often desired that the elastomeric material form an elastic laminate with one or more other layers, such as foams, films, apertured films, and/or nonwoven webs. The elastic laminate generally contains layers that can be bonded together so that at least one of the layers has the characteristics of an elastic polymer. Examples of elastic laminates include, but are not limited to, stretch-bonded laminates and neck-bonded laminates.

The elastic member used in neck-bonded materials, stretch-bonded materials, stretch-bonded laminates, neck-bonded laminates and in other similar laminates can be made from materials, such as described above, that are formed into films, such as a microporous film, fibrous webs, such as a web made from meltblown fibers, spunbond filaments or foams. A film, for example, can be formed by extruding a filled elastomeric polymer and subsequently stretching it to render it microporous.

In one embodiment, the elastic member can be a neck stretched bonded laminate. As used herein, a neck stretched bonded laminate is defined as a laminate made from the combination of a neck-bonded laminate and a stretch-bonded laminate. Examples of necked stretched bonded laminates are disclosed in U.S. Pat. Nos. 5,114,781 and 5,116,662, which are both incorporated herein by reference. Of particular advantage, a neck stretch bonded laminate is stretchable in the machine direction and in a cross machine direction. Further, a neck stretch-bonded laminate can be made with a nonwoven basing that is texturized. In particular, the neck stretched bonded laminate can be made so as to include a nonwoven facing that gathers and becomes bunched so as to form a textured surface. In this manner, the neck stretched bonded laminate can be used to form the entire finger wipe having stretch characteristics in two directions and having a textured surface for cleaning the teeth and gums of a user.

As mentioned, the composition 42 within the pockets 30 may be any desired composition that reacts with an aqueous medium. In addition, the tubular structure 12 may also incorporate the same or another additive. Any material, chemical, or additive commonly applied by cotton ball, swabs, or gauzes, and so forth can be applied with a finger wipe of the present invention. Examples of such additives can include, but are not limited to, medications, lotions, diaper rash ointments, alcohols, oral anesthetics, facial make-up removal agents, cleaning agents, polishing agents, and the like.

Certain compositions and additives are used when the finger wipe is intended as an oral cleaning device. Examples of such dental agents include, but are not limited to alginates, soluble calcium salts, phosphates, fluorides, such as sodium fluoride (NaF) or stannous fluoride ($SnF_2$), and the like. Moreover, mint oils and mint oil mixtures can be applied to a finger wipe of the present invention. For instance, in one embodiment, peppermint oil can be applied to the finger wipe. Moreover, in another embodiment, a mint oil/ethanol mixture can be applied. Components of mint oil (e.g., menthol, carvone) can also be used. Additionally, various whitening agents can be applied to the finger wipe. Examples of whitening agents include peroxides and in situ sources of peroxide, such as carbamide peroxide.

Other additives and compositions can include, but are not limited to, flavoring agents, anti-microbial agents, preservatives, polishing agents, hemostatic agents, surfactants, etc. Examples of suitable flavoring agents include various sugars, breath freshening agents, and artificial sweeteners as well as natural flavorants, such as cinnamon, vanilla and citrus. Moreover, in one embodiment, xylitol, which provides a cooling effect upon dissolution in the mouth and is anti-cariogenic, can be used as the flavoring agent. As stated, preservatives, such as methyl benzoate or methyl paraben, can also be applied to a finger wipe of the present invention. The additives can be applied to the finger wipe as is or they can be encapsulated in order to preserve the additives and/or to provide the additive with time release properties.

Although various embodiments of the invention have been described using specific terms, devices, and methods, such description is for illustrative purposes only. The words used are words of description rather than of limitation. It is to be understood that changes and variations may be made by those of ordinary skill in the art without departing from the spirit or scope of the present invention, which is set forth in the following claims. In addition, it should be understood that aspects of the various embodiments may be interchanged both in whole or in part. Therefore, the spirit and scope of the appended claims should not be limited to the description of the preferred versions contained therein.

What is claimed is:

1. An applicator, comprising;
    a front application panel, and an opposite back panel, said front and back panels forming an open-ended tubular structure;
    said front panel comprising a liquid impermeable material disposed to prevent liquids from migrating into said tubular structure, and an outer liquid permeable cover material coextensive with said liquid impermeable material over said front panel;
    a plurality of discrete pockets formed between said cover material and said liquid impermeable material, said discrete pockets defined by a pattern of unattached portions of said cover material and said liquid impermeable material between attached portions of said cover material and said liquid impermeable material; and
    a composition contained within said pockets, said composition migrating through the entire surface area of said cover material defining said pockets during use of said applicator.

2. The applicator as in claim 1, wherein said tubular structure is sized to fit onto one or more of a user's fingers.

3. The applicator as in claim 1, wherein said front panel comprises a thermoplastic nonwoven cover material attached to said liquid impermeable material at fused portions corresponding to said attached portions such that unfused portions between said cover material and said liquid impermeable material corresponding to said unattached portions define said pockets.

4. The applicator as in claim 3, wherein said pockets have a diameter of generally between about 2 mm to about 10 mm.

5. The applicator as in claim 3, wherein said pockets have a height dimension in a Z direction with respect to a surface plane of said fused portions, said pockets having a width to height ratio of generally between about 1 to about 5.

6. The applicator as in claim 1, wherein said pockets are defined in a discrete zone generally adjacent to a closed end of said tubular structure.

7. The applicator as in claim 6, wherein said cover material further comprises a textured surface in addition to said zone of pockets.

8. The applicator as in claim 7, wherein said textured surface comprises a plurality of additional said pockets between said cover material and said liquid impermeable material that are void of said composition.

9. The applicator as in claim 1, wherein said pockets containing said composition are defined generally uniformly over said cover material.

10. The applicator as in claim 1, wherein said composition comprises a soluble substance that is activated by liquid migrating through said cover material in use of said applicator.

11. The applicator as in claim 10, wherein said composition comprises a powder or granular substance.

12. The applicator as in claim 10, wherein said composition comprises an effervescing flavoring material.

13. The applicator as in claim 1, wherein said composition comprises an encapsulated agent that is released by liquid migrating through said cover material in use of said applicator.

14. The applicator as in claim 13, wherein said applicator is a dental hygiene wipe, and said encapsulated agent is a flavoring agent.

15. The applicator as in claim 1, wherein said applicator is a dental hygiene wipe, and said composition comprises an oral hygiene additive.

16. The applicator as in claim 1, wherein at least one of said front panel or said back panel comprises an elastomeric material.

17. The applicator as in claim 1, wherein said pockets have an elongated shape.

18. The applicator as in claim 1, wherein said pockets have a generally circular shape.

* * * * *